United States Patent [19]

De Jong et al.

[11] Patent Number: 4,832,807
[45] Date of Patent: May 23, 1989

[54] PHOSPHORYLATION OF ALCOHOLS

[75] Inventors: Feike De Jong; Jacob Vermeule, both of Amsterdam, Netherlands

[73] Assignee: Shell Oil Company, Houston, Tex.

[21] Appl. No.: 80,112

[22] Filed: Jul. 31, 1987

[30] Foreign Application Priority Data

Aug. 1, 1986 [GB] United Kingdom ............... 8618861

[51] Int. Cl.$^4$ .............................................. B01J 19/10
[52] U.S. Cl. ......................... 204/157.62; 204/157.73; 204/157.75; 204/157.76; 204/157.78; 204/157.9; 558/112
[58] Field of Search ................. 204/157.62, 157.73, 204/157.75, 157.76, 157.78, 157.9; 558/112

[56] References Cited

U.S. PATENT DOCUMENTS 2,895,973  7/1959  Ready ................................ 558/112
3,573,293  3/1971  Wiese ................................ 558/112

FOREIGN PATENT DOCUMENTS 2842150  4/1980  Fed. Rep. of Germany.
0153844  3/1982  Fed. Rep. of Germany ...... 558/112

*Primary Examiner*—John F. Niebling
*Assistant Examiner*—Ben C. Hsing

[57] ABSTRACT

Phosphorylation of alcohols by contacting the alcohol with a phosphorous sulphide under the impact of ultrasound. The phosporylated produce can be converted into a metal salt, which is a suitable anti-wear additive for lubricating oils.

19 Claims, No Drawings

PHOSPHORYLATION OF ALCOHOLS

FIELD OF THE INVENTION

The present invention relates to a process for the phosphorylation of alcohols with phosphorous sulphide. The product of this phosphorylation is a dithiophosphoric acid derivative which is an intermediate in the preparation of anti-wear additives for lubricating oils.

BACKGROUND OF THE INVENTION

These additives are conventionally prepared in two steps. The first step comprises the phosphorylation of the alcohol with phosphorous sulphide and the second step comprises the treatment of the phosphorylated product with a metal oxide, hydroxide and/or salt.

The first step of this process is slow. In order to obtain commercially feasible reaction rates it may be necessary to heat the reaction mixture to such temperatures that decomposition of the phosphorylation product may occur. In particular in the case of the phosphorylation of phenol or substituted phenols this step is very slow, and on heating, decomposition of the phosphorylated product is likely to occur.

SUMMARY OF THE INVENTION

It has now been found that satisfactory reaction rates can be obtained at low temperatures if ultrasound is applied during the phosphorylation. Accordingly, the present invention provides a process for the phosphorylation of alcohols with a phosphorous sulphide by contacting the alcohol with the phosphorous sulphide under the impact of ultrasound.

The alcohol employed can be any conventional primary, secondary or tertiary alcohol which will react with phosphorous sulphide to form the phosphorylated product. Suitable alcohols include alkanols, such as the pentanols and hexanols, cycloalkanols, such as cyclohexanol, bi- or tri-cycloalkanols, aromatic alcohols, such as phenol and naphtol, arylalkyl alcohols such as benzyl alcohol, all of which may be substituted by one or more alkyl or alkoxy groups; the alcohol can contain from 1 to 25 carbon atoms and equivalent kinds of alcohols. Preferably the alcohol is selected from a $C_{1-20}$ alkanol, $C_{5-8}$ cycloalkanol optionally substituted with one or more $C_{1-4}$ alkyl group, phenol and $C_{1-25}$-alkyl phenol. In case of alkylphenols it was found that the p-alkyl phenols were somewhat more reactive than the O- or m-alkyl phenols. The phosphorous sulphide employed can be any phosphorous sulfide which will react with an alcohol to form a phosphoroylated products, including tetraphosphorous heptasulphide or tetraphosphorous trisulphide and the like, but is preferably phosphorous pentasulphide.

The process according to the invention can be carried out in a diluent. However, it is preferred to work with a reaction mixture which only consists of phosphorous sulphide and the alcohol. The molar ratio between the two reactants may vary within wide ranges, such as from 0.1 to 10 equivalent alcohol per equivalent phosphorous sulphide; it is however preferred to employ substantially stoichiometric quantities of the reactants. This implies that when phosphorous pentasulphide is used the molar ratio of sulphide:alcohol is about 1:4.

The sound intensity influences the reaction rate but limits to the intensity are generally set by economical circumstances. On the one hand the sound intensity should not be too high so that carrying out the process would become very expensive. On the other hand the sound intensity should not be too low so that the reaction is hardly speeded up. To avoid either situation the sound intensity is preferably from 30 to 300 $W/cm^2$. Good results were obtained by using sound frequencies between 10 and 100 kHz.

Ultrasound may be employed during part of the reaction only. However, it appeared that the reaction was only accelerated during the period in which ultrasound was actually applied. Therefore, it is preferred to apply ultrasound during the entire reaction time.

The reaction temperature can be selected from as low as feasible to the temperature where the phosphorylated product gets unstable. Preferably the temperature ranges from 0° to 150° C., in particular from 20° to 110° C. The reaction may be carried out at normal or elevated pressure.

As stated hereinbefore, the phosphorylated product is an intermediate in the preparation of additives for lubricating oils. These additives are the metal salts of such products. Accordingly, the present invention further provides a process for the preparation of metal salts of dithiophosphoric acid derivatives which comprises the phosphorylation of an alcohol with phosphorous sulphide as described above, followed by conversion of the phosphorylated product to the the metal salt by using a metal oxide, hydroxide or by using a base and a metal salt. Preferred metals include group I and group II metals, such as sodium and zinc. In particular zinc salts are preferred. These zinc salts are preferably obtained by converting the phosphorylated product with zinc oxide.

It is further possible to add more than the stoichiometric amount of metal oxide or hydroxide to the phosphorylated product to create a basic metal salt prepared according to the invention. This basic salt is also formed by the reaction of a neutral metal salt of a dithiophosphoric acid derivative with a metal oxide or hydroxide. The formation of the (basic) metal salt from the phosphorylated product and (an excess of) the metal oxide or hydroxide, can also be promoted by the use of ultrasound. This fining, combined with the teaching of the present invention enables a convenient one-step synthesis of a metal salt of dithiophosphoric acid derivative. Accordingly, the present invention further relates to a process for the preparation of a metal salt of a dithiophosphoric acid derivative comprising mixing an alcohol, a phosphorous sulphide and a metal oxide and/or metal hydroxide and subjecting the resulting mixture to ultrasound. The metal salt includes a neutral salt and a basic salt. In this one-step process the alcohol is first phosphorylated, and subsequently the phosphorylated product reacts with the metal oxide or hydroxide.

The metal salts, in particular the zinc salts, of the dithiophosphoric acid derivatives prepared according to the invention are extremely useful as anti-wear additives in a lubricating oil. Therefore, the present invention also provides lubricating oil compositions comprising a major amount of a lubricating base oil and a minor amount of the metal salt of the invention.

The lubricating base oil will conveniently comprise more than 50% of the composition. It can be selected from mineral lubricating oils of varying viscosities, but it also includes a synthetic lubricant, such as conventional ester-type lubricants or polyolefin-type fluids, or a vegetable oil, or a grease.

The lubricating oil compositions can further contain a number of other additives, such as antioxidants, foam inhibitors, corrosion inhibitors, viscosity index improvers, pour paint depressants and the like as can be established by a person of skill in the art.

The invention will be illustrated by means of the following Examples which should not be regarded as limiting it in any way.

EXAMPLE 1

In a vessel 40.5g (110 mmol) of $C_{16-18}$ alkyl phenol was mixed with 6.4g (29 mmol) of phosphorous pentasulphide and the reaction mixture was kept at a temperature of 50° C. The reactants were subjected to ultrasound at a frequency of 20 kHz and a sound intensity of 150 W/cm$^2$. The reaction was stopped after 55 hours, and 38 g of di($C_{16-18}$ aklylphenol)dithiophosphoric acid was obtained after purification of the reaction mixture by filtration (yield 72.8%).

As comparison a similar experiment was carried without the application of ultrasound. The yield of the dithiophosphoric acid derivative was 18.8%.

EXAMPLE 2

Similar procedures as described in Example 1 were carried out but at different temperatures during different reaction times and optionally under interrupted ultrasound application.

In experiment 2a ultrasound was applied in a pulsed fashion: ⅓ s sound, ⅔ s no sound, yielding an ultrasound employment during 33% of the time. In experiment 2b no ultrasound was applied, but the reactor mixture was continuously stirred. Experiments 2c and 2e were carried out under the continuous impact of ultrasound whilst in experiments 2d and 2f, like in 2b, only stirring occurred. The reactions between $C_{16-18}$ alkylphenol and $P_2S_5$ (in stoichiometric amounts) gave the results as indicated in the Table I below.

TABLE 1

| Exper. No. | Ultrasound | | | Reaction | | Yield dithio- phosphoric acid derivative % |
|---|---|---|---|---|---|---|
| | Frequency kHz | Intensity W/cm$^2$ | Duration % react. tune | Temp. C.° | Time h | |
| 2a | 20 | 150 | 30 | 38 | 70 | 15 |
| 2b | — | — | — | 38 | 70 | 2 |
| 2c | 20 | 150 | 100 | 65 | 46 | 75 |
| 2d | — | — | — | 65 | 47 | 34 |
| 2e | 20 | 80 | 100 | 95 | 1.5 | 87 |
| 2f | — | — | — | 95 | 7.5 | 54 |

From the above results it is clearly evident that the application of ultrasound provides substantially accelerated reaction rates and enhanced product yields.

What is claimed is:

1. A process for the phosphorylation of alcohols with a phosphorus sulphide by contacting the alcohol with the phosphorous sulphide and subjecting the resulting mixture to ultrasound.

2. A process according to claim 1, in which the alcohol is a $C_{1-20}$ alkanol, a $C_{5-8}$ cycloalkanol, unsubstituted or substituted with one or more $C_{1-4}$ alkyl groups, phenol, or a $C_{1-25}$-alkyl phenol.

3. A process according to claim 2 in which phosphorous pentasulphide, the frequency of the ultrasound is from 10 to 100 kHz and the intensity of the ultrasound is from 30 to 200W/cm$^2$.

4. A process according to claim 1 in which the phosphorous sulphide is a phosphorous pentasulphide.

5. A process according to claim 1 in which the frequency of the ultrasound is from 10 to 100 kHz, and the ultrasound intensity is from 30 to 300 W/cm$^2$.

6. A process according to claim 1 in which the reaction temperature ranges from 0° to 150° C.

7. A process for the preparation of a metal salt of dithiophosphoric acids derivatives comprising phosphorylation of one alcohol with a phosphorous sulphide according to claim 1 followed by conversion of the phosphorylated alcohol to the metal salt by reacting with a metal oxide or hydroxide or by reacting with a base and a metal salt.

8. A process according to claim 7 in which the phosphorylated alcohol is converted to a zinc salt by reacting with a zinc oxide.

9. A process according to claim 8 in which the alcohol is a $C_{1-20}$ alkanol, a $C_{5-8}$ cycloalkanol, unsubstituted or substituted by one or more $C_{14}$ alkyl groups, phenol, or a $C_{1-25}$ alkylphenol, the phosphorous sulphide is a phosphorus pentasulphide, the frequency of the ultrasound is from 10 to 100 kHz, and the intensity of the ultrasound is from 30 to 300 W/cm$^2$.

10. A process according to claim 7 which is carried out at a temperature in the range from 0° to 100° C.

11. A process according to claim 7 in which the alcohol is a $C_{1-20}$ alkanol, a $C_{5-8}$ cycloalkanol, unsubstituted or substituted by one or more $C_{1-4}$ alkyl groups, phenol, or a $C_{1-25}$ alkylphenol.

12. A process according to claim 7 wherein the phosphorous sulphide is a phosphorous pentasulphide.

13. A process according to claim 7 wherein the frequency of the ultrasound is from 10 to 100 kHz, and the intensity of the ultrasound is from 30 to 300 W/cm$^2$.

14. A process for the preparation of a metal salt of a dithiophosphoric acid derivative comprising mixing an alcohol, a phosphorous sulphide and a metal oxide or hydroxide, and subjecting the resulting mixture to ultrasound.

15. A process according to claim 14 in which a zinc oxide is used.

16. A process according to claim 14 in which the alcohol is a $C_{1-20}$ alkanol, a $C_{5-8}$ cycloalkanol, unsubstituted or substituted by one or more $C_{1-4}$ alkyl groups, phenol, or a $C_{1-25}$ alkylphenol.

17. A process according to claim 14 wherein the phosphorous sulphide is a phosphorous pentasulphide.

18. A process according to claim 17 wherein a zinc salt is prepared in which the phosphorous sulphide is a phosphorous pentasulphide, the frequency of the ultrasound is from 10 to 100 kHz, and the intensity of the ultrasound is from 30 to 300 W/cm$^2$.

19. A process according to claim 14 wherein the frequency of the ultrasound is from 10 to 100 kHz, and the intensity of the ultrasound is from 30 to 300 W/cm$^2$.

* * * * *